US006902753B1

(12) United States Patent
Kemp et al.

(10) Patent No.: US 6,902,753 B1
(45) Date of Patent: Jun. 7, 2005

(54) ACIDIC SOLUTION OF SPARINGLY-SOLUBLE GROUP IIA COMPLEXES

(75) Inventors: Maurice Clarence Kemp, El Dorado Hills, CA (US); Robert B. Lalum, Citrus Heights, CA (US); Zhong Wei Xie, Folsom, CA (US); Michael A. Cunha, Roseville, CA (US); Robert H. Carpenter, Bastrop, TX (US); Zhang Shu, Roseville, CA (US); Yao Yu, Roseville, CA (US); David E. Lewis, Eau Claire, WI (US)

(73) Assignee: Mionix Corporation, Rocklin, CA (US)

( * ) Notice: Subject to any disclaimer, the term of this patent is extended or adjusted under 35 U.S.C. 154(b) by 0 days.

(21) Appl. No.: 09/500,473

(22) Filed: Feb. 9, 2000

Related U.S. Application Data

(63) Continuation-in-part of application No. 09/253,482, filed on Feb. 19, 1999, now abandoned.

(51) Int. Cl.$^7$ .............................................. A23L 3/3454
(52) U.S. Cl. ....................... 426/321; 426/330; 426/331; 426/335; 426/654
(58) Field of Search ................................ 426/321, 330, 426/331, 442, 654, 74, 335, 650, 615, 267

(56) References Cited

U.S. PATENT DOCUMENTS

| | | | | |
|---|---|---|---|---|
| 3,366,490 A | * | 1/1968 | Wagner et al. | 426/330.5 |
| 4,064,284 A | * | 12/1977 | Theron et al. | 426/626 |
| 4,306,516 A | | 12/1981 | Currey | |
| 4,369,197 A | * | 1/1983 | Basel et al. | 426/270 |
| 4,735,802 A | | 4/1988 | Le | |
| 4,781,809 A | | 11/1988 | Falcone, Jr. | |
| 4,830,862 A | * | 5/1989 | Braun et al. | 426/74 |
| 4,983,409 A | * | 1/1991 | Nasu | 426/66 |
| 5,057,220 A | | 10/1991 | Harada | |
| 5,264,017 A | | 11/1993 | Van De Walle | |
| 5,380,430 A | | 1/1995 | Overton et al. | |
| 5,482,528 A | | 1/1996 | Angell | |
| 5,571,336 A | | 11/1996 | Wurzburger et al. | |
| 5,575,974 A | | 11/1996 | Wurzburger et al. | |
| 5,698,107 A | | 12/1997 | Wurzburger et al. | |
| 5,756,051 A | | 5/1998 | Overton et al. | |
| 5,830,838 A | | 11/1998 | Wurzburger et al. | |
| 6,024,994 A | * | 2/2000 | Jacobson et al. | 426/74 |
| 6,086,927 A | * | 7/2000 | Frielich et al. | 426/74 |
| 6,120,822 A | * | 9/2000 | Denvir et al. | 426/320 |
| 6,331,514 B1 | | 12/2001 | Wurzburger et al. | |
| 2002/0168423 A1 | | 11/2002 | Wurzburger | |

FOREIGN PATENT DOCUMENTS

| | | | |
|---|---|---|---|
| AU | WO 9601566 | | 1/1996 |
| EP | 0584976 A | * | 8/1993 |
| GB | 1545788 | | 5/1979 |
| JP | 51-73539 | | 6/1976 |
| JP | 358179436 A | * | 10/1983 |
| JP | 63282117 | | 11/1988 |
| SU | 778 753 | | 11/1980 |
| WO | WO 94/09798 | | 5/1994 |
| WO | WO 99 23896 | | 5/1999 |

OTHER PUBLICATIONS

Leleu, J., Dangerous Chemical Reactions 43. Simple Hydrides, Boranes and Silanes, XP–002123421, 1999, 2 pages.
Saturated Solutions, XP–002123420, 2 pages.
Clifton, C.E., Introduction to the Bacteria, 1950, pp. 270–301.
Shiba, A., et al., Strong Ionized Water Handbook, Sep. 1, 1995, pp. 1–7.
The Watershed, Frequently Asked Questions: Water Ionizers on the Market, www.ionizedwater.com, 1997, pp. 1–3, Spartan Enterprises, Inc.
The Watershed, The Technos by Jupiter, www.ionizedwater.com, 1998, pp. 1–3, Watershed–Spartan Enterprises, Inc.
The Watershed, The Portable Traveler Water Ionizer, www.ionizedwater.com, 1997, pp. 1–2, Spartan Enterprises, Inc.
Natural Solutions, Ionice SDM–2000 Water Ionizer, www.naturalsolutions1.com, 1997, 1 page, Natural Solutions.
Natural Solutions, Ionice SDM–2000 Water Ionizer, www.naturalsolutions1.com, Dec. 4, 1997, pp. 1–3, Natural Solutions.
AITEC, Japanese brochure, AT–2500/AT–5000, 4 pages.
AITEC, Japanese brochure, CL–4, CL–10, 4 pages.
AITEC, Japanese brochure, AT–1000ME, AT–1800ME, AT–2500ME, 4 pages.
U.S. Patent and Trademark Office, Written Opinion, issued Mar. 23, 2001.
U.S. Patent and Trademark Office, International Preliminary Examination Report, issued Jul. 17, 2001.

* cited by examiner

*Primary Examiner*—Milton I. Cano
*Assistant Examiner*—Robert A. Madsen
(74) *Attorney, Agent, or Firm*—Jackson Walker L.L.P.

(57) ABSTRACT

An acidic solution of sparingly-soluble Group IIA complexes ("AGIIS"), its preparation and its uses. The AGIIS can be prepared by mixing a mineral acid (such as sulfuric acid), and a Group IIA hydroxide (such as calcium hydroxide) or a Group IIA salt of a dibasic acid (such as calcium sulfate), or a mixture of the two Group IIA compounds, followed by removing the solid formed. The various uses include cleaning, food production, decontamination, bioremediation, agricultural application, medical application, and detoxification of substances.

5 Claims, 1 Drawing Sheet

ACIDIC SOLUTION OF SPARINGLY-SOLUBLE GROUP IIA COMPLEXES

This application is a continuation-in-part of an application filed Feb. 19, 1999, Ser. No. 09/253,482, now abandoned, the entire content of which is hereby incorporated by reference.

BACKGROUND

This invention relates to an acidic solution of sparingly-soluble Group IIA-complexes ("AGIIS"), its preparations, and its uses.

In the late 80's and early 90's, researchers in Japan developed strong ionized water ("SIW") as disinfectants. The SIW was established as water with pH 2.7 or less, having an oxidation-reduction potential of 1,000 mv or more, and chlorine concentration of 0.8 ppm or more. The SIW is prepared by electrolysis of water.

Electrolysis of tap water has also been used to produce "strong acid water" and "strong alkali water" both of which were claimed to have antiseptic properties.

U.S. Pat. No. 5,830,838 to Wurzburger, et al. describes a solution for cleaning metal surfaces. The solution is prepared by mixing calcium hydroxide and potassium hydroxide with equivalent of sulfuric acid in water then passing the solution through a 10 micron filter. The resulting concentrate can be diluted depending on the degree of surface oxidation of the metal to be treated.

U.S. Pat. No. 5,895,782 to Overton, et al. describes a solution for cleaning metal surfaces particularly non-ferrous alloys such as copper, brass and high strength aluminum alloys. The solution is prepared by mixing $Ca(OH)_2$ and KOH with equivalent sulfuric acid in water then passing the solution through a 10 micron filter. The resulting concentrate can be used full strength or diluted depending on the degree of surface oxidation of the metal to be treated.

International Publication WO 94/09798 describes a pharmaceutical composition for treatment of disease, injury and other disorders. The pharmaceutical composition comprises a complex of a calcium-containing component and a sulfate-containing component in a pharmaceutically acceptable carrier. The reference teaches the isolation from natural materials, such as peat, the inorganic compositions. The inorganic preparations comprise an alkaline, aqueous or organic, or mixture thereof, extract of peat. Peat is extracted with aqueous solutions, organic solutions or water-miscible organic solvents at temperature from below room temperature up to the boiling point of the solvents. The preferred extracting solvents are those having a pH of at least 9. Biologically active constituents of fractionated peat preparations were identified as $CaSO_4 \cdot 2H_2O$ (gypsum), $CaSO_4 \cdot K_2SO_2SO_4 \cdot H_2O$ (syngenite, also referred to as the double salt of gypsum) and $K_3Na(SO_4)_2$ (apthitalite) by X-ray powder diffraction analysis. The reference also describes the synthesis of syngenite.

Chemists describe and measure the ability of a substance to donate protons [$H^+$] to a chemical reaction as the pKa of that substance where

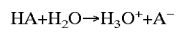

Although a hydronium ion is usually represented by $H^-$ or $H_3O^+$, but its true formula is not certain. The aggregate could be $H_5O_2^+$, $H_7O_3^+$, or even $H_9O_4^+$.

Positively charged water has the ability to donate protons [$H^+$]. The donation of a proton is usually an intermediate step in any acid hydrolysis reaction. Acids are usually the chemical reagent used to donate protons in an aqueous solution. If the water could be the source of the [$H^+$], then there would be fewer unwanted by-products (toxics) from the reactions and there would be less hazard associated with these products use.

A strong acid is used to neutralize and remove the lime, or quicklime, from the brick and mortar. A strong acid, such as hydrochloric acid, also known as muriatic acid, is also used to clean hard water spots on shower stalls, windows, glass, toilets, urinals, mirrors and other surfaces. Hydrochloric acid is used to de-scale water towers and heat exchangers and to adjust the pH of the waste water effluent. A full strength mineral acid, such as hydrochloric acid, is extremely corrosive to many substances, including metals. In addition, hydrochloric acid at a low pH of 0.5 or so will burn a human skin in seconds. The acid is also very harmful in that it emits fumes irritating to the mucous membrane. If left near other chemicals, like bleach, hydrochloric acid will interact with them, even through a typical plastic bottle.

It is thus desirable to be able to have a source of "acidity," or $H_3O^+$, without these unwanted disadvantages and be able to reduce environmental and safety hazards associated with acid hydrolysis. Preferably, this source of "acidity" should be able to prevent re-contamination following decontamination, not induce bacterial resistance, not alter the taste, color or smell of treated foodstuffs, not create any odor, effective in water in a wide range of temperatures, relatively free of danger when overdosed, can be neutralized after use, not carcinogenic or mutagenic, non-toxic, almost harmless in water and the environment, environmentally friendly, and can be stored for a long period of time without decomposition or turning into hazardous compound.

The control of microbial growth is necessary in many practical situations, and significant advances in agriculture, medicine and food science have been made through study of this area of microbiology. "Control of growth" means to prevent growth of microorganisms. This control is effected in one of two basic ways: (1) By killing microorganisms; or (2) by inhibiting the growth of microorganisms. Control of growth usually involves the use of physical or chemical agents which either kill or prevent the growth of microorganisms. Agents which kill cells are called "cidal" agents; agents which inhibit the growth of cells, but without killing them, are referred to as "static" agents. Thus the term "bactericidal" refers to killing bacteria and "bacteriostatic" refers to inhibiting the growth of bacterial cells. A "bactericide" kills bacteria, a "fungicide" kills fungi. "Sterilization" is the complete destruction or elimination of all viable organisms in or on an object being sterilized. The object is either sterile or not, there are no degrees of sterilization. Sterilization procedures involve the use of heat, radiation or chemicals, or physical removal of microorganisms.

Microorganisms tend to colonize and replicate on different surfaces resulting in adherent heterogenous microbial accumulations termed "biofilms." Biofilms may form on surfaces of food substances, feed substances, and instrumentations. The microorganisms in the biofilms may include bacteria, fungi, viruses, and protozoans. Since food safety is a national priority, any product that can help by solving a multitude of problems associated with food production is desirable. Removal and control of biofilms which harbor dangerous microbial contamination is a sanitation goal that needs to be achieved. It is also desirable to be able to safely decontaminate water and nutriment by lowering pH to levels where contaminants would react and organisms cannot live.

As used herein, the term "nutriment" means something that nourishes, heals, or promotes growth and repair the natural wastage of organic life. Thus, food for a human and feed for an animal are all examples of nutriment. Other examples of nutriment include beverages, food additive, feed additive, beverage additive, food supplement, feed supplement, beverage supplement, seasoning, spices, flavoring agent, stuffing, food dressing, pharmaceutical, biological product, and others. The nutriment can be of plant origin, animal origin, or synthetic. Current sanitizing, disinfectants and pesticides products on the market for these uses contain residues of chlorine, ammonia, organic iodine, metal salts and other deleterious residues. It is desirable to have a way that would preclude these residues by promoting acid hydrolysis without the presence of deleterious chemicals. Additionally, this method should generate few hazardous volatile gases. Importantly, it is highly desirable to have a composition that can control and the growth of, and kill, microorganisms and, at the same time, destroy the products, such as toxins, generated by, or associated with, the microorganisms.

SUMMARY

The present invention involves an acidic, or low pH, solution of sparingly-soluble Group IIA-complexes ("AGIIS"), its preparation, and its uses. One embodiment of the present invention pertains to highly acidic solution prepared by mixing or blending a mineral acid with a Group IIA hydroxide or a Group IIA salt of a dibasic acid, or a combination of the Group IIA hydroxide and Group IIA salt of a dibasic acid. Still other aspects of the present invention pertain to different methods to promote the safe, clean, and environmentally sensitive ways of chemical production, pharmaceutical production, cleaning, food production, decontamination, bioremediation, agricultural application, medical application, and detoxification as well as decontamination of a wide variety of substances.

DETAILED DESCRIPTION

Figure 1:
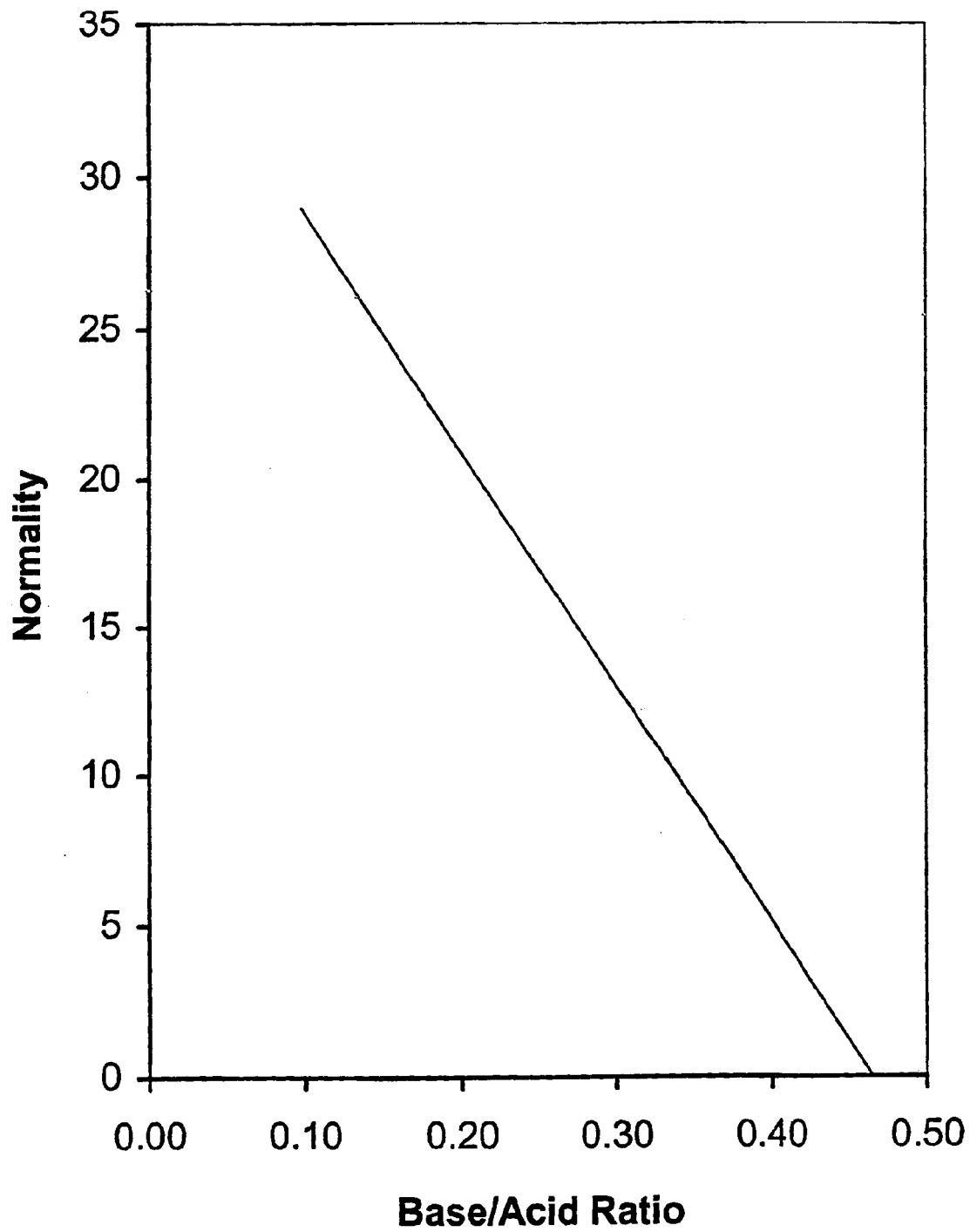
FIG. 1 shows the relation of the desired final acid normality of AGIIS and the mole ratio of calcium hydroxide to sulfuric acid, given in moles of calcium hydroxide per mole of sulfuric acid.

One aspect of the present invention pertains to an acidic, or low pH, solution of sparingly-soluble Group IIA-complexes ("AGIIS"). The solution may have a suspension of very fine particles. The term "low pH" means the pH is below 7, in the acidic region. The AGIIS of the present invention with a certain acid normality does not have the same dehydrating behavior as sulfuric acid solution saturated with calcium sulfate having the same acid normality. In other words, the AGIIS of the present invention with a certain acid normality does not char sucrose as readily as does a saturated solution of calcium sulfate in sulfuric acid having the same normality. Further, the AGIIS is non-volatile at room temperature. It is less corrosive to a human skin than sulfuric acid saturated with calcium sulfate having the same acid normality. Not intending to be bound by the theory, it is believed that one embodiment of AGIIS comprises near-saturated, saturated, or super-saturated calcium, sulfate anions or variations thereof, and/or complex ions containing calcium, sulfates, and/or variations thereof.

The term "complex," as used herein, denotes a composition wherein individual constituents are associated. "Associated" means constituents are bound to one another either covalently or non-covalently, the latter as a result of hydrogen bonding or other inter-molecular forces. The constituents may be present in ionic, non-ionic, hydrated or other forms.

The acidic solution of sparingly-soluble Group IIA-complex salt ("AGIIS") can be prepared in several ways. Some of the methods involve the use of Group IA hydroxide but some of syntheses are devoid of the use of any added Group IA hydroxide, although it is possible that a small amount of Group IA metal may be present as "impurities." The preferred way of manufacturing AGIIS is not to add Group IA hydroxide to the mixture. As the phrase implies, AGIIS is highly acidic, ionic, with a pH of below about 2.

Wurzburger, et al. in U.S. Pat. No. 5,830,838 describes an acidic solution prepared by the "calcium-hydroxide/potassium-hydroxide method." The solution is produced by first adding two moles of concentrated sulfuric acid (93%) to 2 liters of de-ionized water. Separately, an aqueous solution of base is prepared by adding one mole of calcium hydroxide (hydrated lime) and two moles of potassium hydroxide to 20 liters of de-ionized water with stirring. The acid solution is then mixed with the base solution. The mixture is then filtered through a 10 micron filter to remove particles of calcium sulfate or potassium sulfate of eleven microns or larger. The resulting concentrate can be used full strength or diluted with water depending on the metal surfaces to be treated. Sodium hydroxide may be used in place of potassium hydroxide. Hydrated calcium oxide may be used in place of calcium hydroxide. Another source of the base is calcium metal. In either case and as one embodiment of this application, the resultant solution is a highly acidic solution. This highly acidic solution can be diluted with water to adjust its pH to a desired higher value, i.e. less acidic.

Another way of preparing the acidic solution is by the "calcium-metal method" which involves reacting concentrated sulfuric acid with calcium metal followed by filtration. One mole of concentrated sulfuric acid was diluted with 40 moles of de-ionized water. Then, one mole of calcium metal turnings was slowly added with stirring into the solution of sulfuric acid. The stirring was continued until essentially all metal had dissolved. The resultant mixture was allowed to settle for about 5 to 6 hours before the supernatant was filtered through a 10 micron filter. The concentrate thus obtained had a pH value of about 0.5. This concentrate of hydronium ions was then diluted with de-ionized water to the desired pH value, such as pH of about 1 or about 1.8.

Then, there is the "calcium-hydride method" which involves reacting concentrated sulfuric acid and calcium hydride in water. One mole of concentrated sulfuric acid was diluted with 40 moles of de-ionized water. With agitation, 1 mole of calcium hydride was slowly added to the solution of sulfuric acid. The agitation was continued until the calcium hydride has essentially all dissolved. After the dissolution, the mixture was then allowed to settle for about 5 to 6 hours, at that time the supernatant was filtered through a 10 micron filter. The concentrate thus obtained had a pH value of about 0.1 to about 0.2, and can be further diluted.

One product from the "calcium-metal method" or "calcium-hydride method" having a pH of from −0.2 to −0.3, and from 1.4 to 1.5 acid normality gave the following analyses: Ca, 763 ppm; $SO_4$, 84533 ppm; Na, 4.76 ppm; K, 3.33 ppm; and Mg, 35.7 ppm.

The "calcium-metal method" and the "calcium-hydride method" have certain drawbacks. In each of these methods, thermal control is very difficult to achieve because of the large amount of heat generated when concentrated sulfuric acid is reacted with either calcium metal or calcium hydride. The difficulties in thermal control of the reactions cause the reactions to be difficult to reproduce and hard to control.

The preferred method of preparing AGIIS involves mixing a mineral acid with a Group IIA hydroxide, or with a Group IIA salt of a dibasic acid, or with a mixture of the two Group IIA materials. In the mixing, a salt of Group IIA is also formed. Preferably, the starting Group IIA material or materials selected will give rise to, and form, the Group IIA salt or salts that are sparingly soluble in water. The preferred mineral acid is sulfuric acid, the prefered Group IIA hydroxide is calcium hydroxide, and the prefer Group IIA salt of a dibasic acid is calcium sulfate. Other examples of Group IIA salt include calcium oxide, calcium carbonate, and "calcium bicarbonate."

Thus, for example, AGIIS can be prepared by mixing or blending starting materials given in one of the following scheme with good reproducibility:

(1) $H_2SO_4$ and $Ca(O)_2$;
(2) $H_2SO_4$, $Ca(OH)_2$, and $CaCO_3$;
(3) $H_2SO_4$, $Ca(OH)_2$, $CaCO_3$, and $CO_2$ (gas);
(4) $H_2SO_4$ and $CaCO_3$;
(5) $H_2SO_4$, $CaCO_3$, and $Ca(OH)_2$;
(6) $H_2SO_{41}$ $CaCO_3$, and $CO_2$ (gas);
(7) $H_2SO_4$ and $CaSO_4$;
(8) $H_2SO_4$, $Ca(OH)_2$, and $CaSO_4$;
(9) $H_2SO_4$, $CaSO_4$, and $CaCO_3$;
(10) $H_2SO_4$, $CaSO_4$, $CaCO_3$, and $Ca(OH)_2$;
(11) $H_2SO_4$, $CaSO_4$, $CaCO_3$, and $CO_2$ (gas); and
(12) $H_2SO_4$, $CaSO_4$, $CaCO_3$, $CO_2$ (gas), and $Ca(OH)_2$.

Thus, preferably, AGIIS is prepared by mixing calcium hydroxide with concentrated sulfuric acid, with or without an optional Group IIA salt of a dibasic acid (such as calcium sulfate) added to the sulfuric acid. The optional calcium sulfate can be added to the concentrated sulfuric acid prior to the introduction of calcium hydroxide into the blending mixture. The addition of calcium sulfate to the concentrated sulfuric acid appears to reduce the amount of calcium hydroxide needed for the preparation of AGIIS. Other optional reactants include calcium carbonate and gaseous carbon dioxide being bubbled into the mixture. Regardless of the use of any optional reactants, it was found that the use of calcium hydroxide is desirable.

One preferred method of preparing AGIIS can be described briefly as: Concentrated sulfuric acid is added to chilled water (8°–12° C.) in the reaction vessel, then, with stirring, calcium sulfate is added to the acid in chilled water to give a mixture. Temperature control is paramount to this process. To this stirring mixture is then added a slurry of calcium hydroxide in water. The solid formed from the mixture is then removed. This method involves the use of sulfuric acid, calcium sulfate, and calcium hydroxide, and it has several unexpected advantages. Firstly, this reaction is not violent and is not exceedingly exothermic. Besides being easy to control and easy to reproduce, this reaction uses ingredients each of which has been reviewed by the U.S. Food and Drug Administration ("U.S. FDA") and determined to be "generally recognized as safe" ("GRAS"). As such, each of these ingredients can be added directly to food, subject, of course, to certain limitations. Under proper concentration, each of these ingredients can be used as processing aids and in food contact applications. Their use is limited only by product suitability and Good Manufacturing Practices ("GMP"). The AGIIS so prepared is thus safe for animal consumption, safe for processing aids, and safe in food contact applications. Further, the AGIIS reduces biological contaminants in not only inhibiting the growth of, and killing, microorganisms but also destroying the toxins formed and generated by the microorganisms. The AGIIS formed can also preserve, or extend the shelf-life of, consumable products, be they plant, animal, pharmaceutical, or biological products. It also preserves or improves the organoleptic quality of a beverage, a plant product or an animal product. It also possesses certain healing and therapeutic properties.

The sulfuric acid used is usually 95–98% FCC Grade (about 35–37 N). The amount of concentrated sulfuric acid can range from about 0.05 M to about 18 M (about 0.1 N to about 36 N), preferably from about 1 M to about 5 M. It is application specific. The term "M" used denotes molar or moles per liter.

Normally, a slurry of finely ground calcium hydroxide suspended in water (about 50 of W/V) is the preferred way of introducing the calcium hydroxide, in increments, into the a stirring solution of sulfuric acid, with or without the presence of calcium sulfate. Ordinarily, the reaction is carried out below 40° C., preferably below room temperature, and more preferably below 10° C. The time to add calcium hydroxide can range from about 1 hour to about 4 hours. The agitation speed can vary from about 600 to about 700 rpm, or higher. After the mixing, the mixture is filtered through a 5 micron filter. The filtrate is then allowed to sit overnight and the fine sediment is removed by decantation.

The calcium hydroxide used is usually FCC Grade of about 98% purity. For every mole of concentrated acid, such as sulfuric acid, the amount, in mole, of calcium hydroxide used is application specific and ranges from about 0.1 to about 1.

The optional calcium carbonate is normally FCC Grade having a purity of about 98%. When used with calcium hydroxide as described above, for every mole of concentrated acid, such as sulfuric acid, the amount, in mole, of calcium carbonate ranges from about 0.001 to about 0.2, depending on the amount of calcium hydroxide used.

The optional carbon dioxide is usually bubbled into the slurry containing calcium hydroxide at a speed of from about 1 to about 3 pounds pressure. The carbon dioxide is bubbled into the slurry for a period of from about 1 to about 3 hours. The slurry is then added to the reaction vessel containing the concentrated sulfuric acid.

Another optional ingredient is calcium sulfate, a Group IIA salt of a dibasic acid. Normally, dihydrated calcium sulfate is used. As used in this application, the phrase "calcium sulfate," or the formula "$CaSO_4$," means either anhydrous or hydrated calcium sulfate. The purity of calcium sulfate (dihydrate) used is usually 95–98% FCC Grade. The amount of calcium sulfate, in moles per liter of concentrated sulfuric acid ranges from about 0.005 to about 0.15, preferably from about 0.007 to about 0.07, and more preferably from about 0.007 to about 0.04. It is application specific.

From experimental data, a slope was generated showing the ratio of calcium hydroxide to concentrated sulfuric needed for a desired final acid normality of AGIIS. See, FIG. 1.

The slope in FIG. 1 was created from two pairs of data points found by titrating a given amount of acid to a desired final acid normality. The accuracies were determined chemically. The final acid normality of the finished product ranges from about 1.2 to about 29. To produce one liter of 1.2 N AGIIS, it was found that for every mole of concentrated sulfuric acid, 0.45 moles of Ca(OH)$_2$ was required. To produce one liter of 27 N AGIIS, it was found that for every mole of concentrated sulfuric acid, 0.12 moles of Ca(OH)$_2$ was required. The data were then plotted onto a graph where the Y-axis represents final acid normality and the X-axis represents moles of Ca(OH)$_2$/1 mole of concentrated sulfuric acid, where $X_1=0.45$, $X_2=0.12$, $Y_1=1.2$, and $Y_2=27$. The slope of the line was found by using the equation $(Y_1-Y_2)/(X_1-X_2)$, which was −78.18. The line can be represented by the equation Y=mX+b, where mX is the slope, and b is the Y intercept. The highest acid normality was 36.65, thus the equation is:

$$Y=-78.18X+36.65$$

This slope is useful for the preparation of an AGIIS solution having a desired final acid normality.

Broadly, the method of preparing AGIIS having a desired final acid normality involves the steps given below. The calculations are based on a 1 liter of final volume of AGIIS, the amounts of acid (concentrated sulfuric acid) and base (calcium hydroxide) are in moles, the ratio of base to acid is the number of moles of base (calcium hydroxide) for every mole of acid (concentrated sulfuric acid). The steps are:

(a) Determining the amount of mineral acid (such as concentrated sulfuric acid), in moles, needed to produce AGIIS having the desired final acid normality ("N") by using a relationship given by the following equation:

$$E_1=(N/2)+(N/2+B)$$

in which $E_1$ is the amount of acid, in moles, required before correcting for purity, or purity adjustment; N is the desired final acid normality; and B is the mole ratio of the Group IIA hydroxide to the mineral acid needed to obtain the AGTIIS having N, and B is derived from a pre-plotted curve depicting the relationship of the mineral acid and the Group IIA hydroxide for a desired final N;

(b) making purity adjustment for the mineral acid used. The correction for the purity of the acid used is accomplished by the equation:

$$E_2=E_1/C$$

in which $E_2$ is the amount of acid, in moles, required after correcting for purity of the acid used, or purity adjustment; $E_1$ is as defined above; and C is purity adjustment factor for the acid used. For concentrated sulfuric acid, the average acid strength is about 96.5%, and thus C is 0.965;

(c) determining the amount of water, in ml, that has to be added to the acid whose acid solution will then, after the reaction, give the desired final acid normality N. The relationship is as follows:

$$G=J-E_2-I$$

in which G is the amount of water required to be added to the mineral acid solution to get the desired final acid normality; J is the final volume of the aqueous mineral acid solution; I is the volume amount of Group IIA hydroxide needed (see, below); and $E_2$ is as defined above;

(d) adding G to $E_2$ to give the final aqueous solution of the mineral acid, in which both G and $E_2$ are as defined above;

(e) determining the amount of base, (such as calcium hydroxide), in moles, needed for the reaction to produce AGIIS having the desired final acid normality N. For example, from the straight line in FIG. 1, the mole ratio of Ca(OH)$_2$ to concentrated H$_2$SO$_4$ to achieve a certain final acid normality can be determined.

the amount of the base, in moles, needed is:

$$F_1=N/2\times B$$

in which $F_1$ is the amount of base, in moles, needed; and N and B are as defined above;

(f) the correction for the purity of the base used is accomplished by the equation:

$$F_2=F_1/D$$

in which $F_2$ is the amount of base, in moles, required after correcting for purity of the base used, or purity adjustment; and D is purity adjustment factor for the base used.

The average purity of sodium hydroxide is about 98%, and, thus, D, in this case, is 0.98;

(g) determining the amount of water, in ml, needed to make the slurry of base. The relationship is as follows:

$$H=F_2\times 1.5$$

in which H is the volume of water, in ml, needed to make the slurry of base which, in turn, will give AGIIS with the desired final acid normality N. $F_2$ is as defined above. The H given is an approximation and should be adjusted to a desired final weight volume. Thus, for example, 50 g of base should be adjusted to a final volume of 100 ml because the slurry used is a 50:50 mixture of solid and water;

(h) determining the volume, in ml, of the base slurry or solution to be added to the acid solution to give AGIIS with the desired final acid normality N. The relationship can be expressed as:

$$I=F_2\times 2$$

in which I is the volume, in ml, of the slurry or solution of base to be added to the acid solution; and $F_2$ is as defined above;

(i) adding H to $F_2$ to give the final aqueous slurry or solution of the base, in which both H and $F_2$ are as defined above;

(j) adding the final aqueous solution or slurry or the base of (i) to the final aqueous solution of mineral acid of (d);

(k) allowing the final aqueous solution or slurry of the base and the final aqueous solution of mineral acid (j) to react; and (l) removing solid formed from the reaction of (k).

In the event that CaSO$_4$ is used for the reaction by adding it to the solution of concentrated H$_2$SO$_{4}$, the amount of CaSO$_4$, in grams per liter of solution based on final volume, has the following relationship:

| Final AGIIS Acid Normality N | Amount of CaSO$_4$ in g/l |
|---|---|
| 1–5 | 5 |
| 6–10 | 4 |
| 11–15 | 3 |

-continued

| Final AGIIS Acid Normality N | Amount of CaSO$_4$ in g/l |
|---|---|
| 16–20 | 2 |
| 21–36 | 1 |

The AGIIS obtained could have an acid normality range of from about 0.05 to about 31; the pH of lower than 0; boiling point of from about 100 to about 106° C.; freezing point of from about −8° C. to about 0° C.

AGIIS obtained from using the reaction of $H_2SO_4$/Ca(OH)$_2$/CaSO$_4$ had the following analyses (average):

AGIIS With Final Acid Normality of 1.2 N, pH of −0.08 $H_3O^+$, 2.22%; Ca, 602 ppm; SO$_4$, 73560 ppm; K, 1.36 ppb; impurities of 19.68 ppm, and neither Na nor Mg was detected.

AGIIS With Final Acid Normality of about 29 N, pH of about −1.46

$H_3O^+$, 30.68%; Ca, 52.9 ppm; SO$_4$, 7356000 ppm; K, 38.02 ppb; and neither Na nor Mg was detected.

Besides concentrated sulfuric acid, other polyprotic acids, such as phosphoric acid, phosphorous acid, chloric acid, iodic acid, or others can be used.

Likewise, aqueous solutions of other alkalines or bases, such as Group IA hydroxide solution or slurry and Group IIA hydroxide solution or slurry can be used. Groups IA and IIA refer to the two Groups in the periodical table. The use of Group IIA hydroxide is preferred. Preferably, the salts formed from using Group IIA hydroxides in the reaction are sparingly-soluble in water. It is also preferable to use only Group IIA hydroxide as the base without the addition of Group IA hydroxide.

After the reaction, the resultant concentrated acidic solution with a relatively low pH value, typically below pH 1, can then be diluted with de-ionized water to the desired pH value, such as pH of about 1 or about 1.8.

However, it is sometimes desirable not to prepare a very concentrated AGIIS solution and then dilute it serially to obtain the solution having the desired final acid normality. It is often desirable to prepare a solution of AGIIS having a desired final pre-determined acid normality according to the method described in this application so that not much dilution of the product is required before use.

As discussed above, AGIIS has relatively less dehydrating properties (such as charring sucrose) as compared to the saturated solution of CaSO$_4$ in the same concentration of $H_2SO_4$. Further, the stability and non-corrosive nature of the AGIIS of the present invention can be illustrated by the fact that a person can put his or her hand into this solution with a pH of less than 0.5 and, yet, his or her hand suffers no irritation, and no injury. If, on the other hand, one places his or her hand into a solution of sulfuric acid 0f of less than pH 0.5, an irritation would occur within a relatively short span of time. A solution of 28 N of sulfuric acid saturated with calcium sulfate will cause chemical burn to a human skin after a few seconds of contact. In contrast, AGIIS solution of the same normality would not cause chemical burn to a human skin even after in contact for 5 minutes. The AGIIS of the present invention does not seem to be corrosive when being brought in contact with the environmental protective covering of plants (cuticle) and animals (skin). AGIIS is non-volatile at room temperature. Even as concentrated as 29 N, the AGIIS has no odor, does not give off fumes in the air, and is not irritating to a human nose when one smells this concentrated solution.

A "biological contaminant" is defined as a biological organism, or the product of biological organism, such as toxin, or both, all of which contaminate the environment and useful products. This biological contaminant results in making the environment or product hazardous.

Biological contaminants, such as bacteria, fungi, mold, mildew, spores, and viruses have potentially reactive substances in their cell wall/membranes; however, they hide in cells (viruses and some bacteria) and/or secrete biofilms (most bacteria, fungi, mold and mildew) to protect them from the environment.

Bacterial form or elaborate intracellular or extracellular toxins. Toxin is a noxious or poisonous substance that: (1) is an integral part of the bacteria; (2) is an extracellular product (exotoxin) of the bacteria; or (3) represents a combination or the two situations, formed or elaborated during the metabolism and growth of bacteria. Toxins are, in general, relatively complex antigenic molecules and the chemical compositions are usually not known. The harmful effects of bacteria come not only from the bacteria themselves, but also from the toxins produced by bacteria. Toxins produced by bacteria are just as, if not more, hazardous to the product than the bacteria themselves. Ordinary disinfectants, such as quaternary ammonium compounds, will kill bacteria but have no effect on bacterial toxins and endotoxins. In fact, many disinfectants actually contribute to the endotoxins problems by causing their release from the bacteria. The bacterial toxins and endotoxins can cause serious adverse effects in human and animals. Endotoxins are the major cause of contamination in food products, in the production of pharmaceuticals, medical devices, and other medical products. Thus, while "decontaminating" a product infested with bacteria, it is not enough to simply kill or reduce the number of bacteria. To get a safe and decontaminated product, the toxins and endotoxins of the bacteria must also be destroyed. Neither killing the microorganism alone nor destroying the toxins alone is enough in the real world. To be useful, when reducing biological contaminants in a nutriment or in an equipment, the growth of biological organisms must be controlled and reduced, and, at the same time, the product of biological organisms (such as toxins) must be removed and/or destroyed.

The outer covering, i.e. epidermis, of animals and cuticle of plants resist the growth and/or entry of the above microorganisms into the interior of the complex organism. One of the microbial growth prevention methods used by plants and animals is the maintenance of a surface pH or secretion of a coating that is not conducive to the attachment and propagation of micro-organisms. After a plant product is harvested or an animal product processed, these products loose the ability to resist the infestation of micro-organisms. By spraying the composition of the present invention plus defined additives on fruits, vegetables, and whole plants post harvest or washing or packing animal products in the composition, the growth and propagation of micro-organisms in these products can be reduced. If plant or animal products are packed in the composition an additional benefit is realized when the product is heated because the pH of the composition, and in turn the product, goes down giving the added potential of the composition of destroying any micro-organisms, their toxins or other harmful substances.

The composition of the present invention was found to be a "preservative." The composition is not corrosive; however, it car create an environment where destructive micro-organisms cannot live and propagate, thus prolong the shelf-life of the product. The utility of this method of preservation is that additional chemicals do not have to be added to the food or other substance to be preserved because the inherent low pH of the mixture is preservative. Since preservative chemicals do not have to be added to the food substance, taste is improved and residues are avoided. Organoleptic testing of a number of freshly preserved and previously preserved food stuffs have revealed the addition of composition improves taste and eliminates preservative flavors. The term "organoleptic" means making an impression based upon senses of an organ or the whole organism. In another use, the composition was added to various food dressing, fresh juices and fermented beverages (wine). The resulting taste was unanimously judged better than the starting or control beverage. Use of the composition both as a preservative and taste enhancer for food and beverages will produce a safer and more desirable product. Additionally the composition can be added to biologics, pharmaceuticals and other preservative sensitive products to enhance their safety and extend shelf life. It can also be used as an ingredient to adjust product pH.

Conventional cleaning of biopharmaceutical and vaccine equipment is always problematical. Bioreactor vessels, where genetically altered yeast and bacteria produce biopharmaceutical products, are very sensitive to residues left during the cleaning process. The adduct or composition of the present invention is extremely useful in the primary cleaning of these vessels following production termination and for final cleaning and rinsing just prior to reestablishing the culture in the reactor vessel. The composition's ability to completely remove residues will insure the success of the culture and eliminate the possibility of contamination in the biopharmaceutical or vaccine product.

Another field of manufacturing where cleaning is critical is in the precision injection molding of plastic and composite materials for critical use parts in medical devices and other industrial products. The composition of the present invention can clean the injection molds quickly and efficiently between runs without damaging the molds or leaving residues which can cause defects in the product. Additionally, the composition could be used to remove excess materials from the parts and acid etch or clean parts prior to assembly and welding. The composition of the present invention is useful to clean the surface of non metallic parts to be chemically, heat or ultrasonically welded. If the device is wet packaged, i.e. suture material, then the composition can be used as a packaging preservative.

Agricultural applications for the composition of the present invention are of special interest. The ability to manipulate the pH of hydroponic plant production water will influence fruit production and disease control. Synchronization of harvest and completeness of harvest can be aided by the composition. Olive, nut and some fruit trees are harvested by mechanical shaking. This shaking procedure must occur several times because the fruit and stem do not always ripen at the same time. Spraying the tree with the composition prior to harvest activities can cause the stems and produce to mature rapidly. Only one or two shaking procedures will be required to completely harvest the produce, thus reducing harvest cost and damage to the trees.

Bacteria, fungus, yeast and molds can reduce plant yields or effect the quality of crops near, at, or post harvest. The composition of the present invention can be useful in preventing mold and mildew when crops in production are subjected to wet conditions. This is especially true in corn, maize and other grain sorghram production. Grapes destined for raisin production are harvested and left to dry in the field on paper or cloth tarps between the vines. If wet weather persists the raisins will mold during the drying process resulting in an unusable product. Spraying the composition on the grapes prior to harvest, dipping the clusters during harvest, treating the tarps, spraying the drying clusters, and washing the raisins prior to packing will result in raisins free of mold. The same methods can be used to assure uniformity of grapes during wine making. The composition of the present invention can be used to control pH and adjust taste of wine and other fermented beverages.

The same use of the composition of the present invention can be made when storing grains. Mold, mildew and other fungal infestations of stored grains produce mycotoxins. These mycotoxins are very harmful to animals that consume contaminated grains. Mycotoxin intoxication results in organ damage, decreased production, or death. Chemicals containing mercury and iodine are used to preserve planting seed, but there are no preservatives for grains destined for food or feed which do not leave harmful residues. Grains at harvest, during processing or in storage could be exposed to the composition, with or without additives, to create an environment where these organisms would not grow on the grain or in the storage container.

Specific field applications for military use are numerous. The primary application is in the decontamination of drinking water. Current methods for individual drinking water decontamination consist of placing iodine tablets into a canteen of water and waiting a period of time. If a small amount of the composition of the present invention is added to the water, time for disinfection would be significantly reduced and there would be no need for iodine tablets. Additional applications for field living would include field waste decontamination, cooking liquid for food sources of questionable sanitary status, first aid irrigation solution for wounds and decontamination, dilution and clean up of toxic or dangerous substance spills, and equipment cleaning and decontamination. This is especially important when food service under field conditions does not always allow for hot water cleaning of equipment.

The following examples are provided to further illustrate this invention and the manner in which it may be carried out. It will be understood, however, that the specific details given in the examples have been chosen for purposes of illustration only and not be construed as limiting the invention. Unless otherwise defined, the amount of each ingredient or component of the present invention is based on the weight percent of the final composition.

EXAMPLE 1

Preparation of 1.2–1.5 N AGIIS ($H_2SO_4Ca(OH)_2$)

An amount of 1055 ml (19.2 moles, after purity adjustment and taking into account the amount of acid neutralized by base) of concentrated sulfuric acid (FCC Grade, 95–98% purity) was slowly added with stirring, to 16.868 L of RO/DI water in each of reaction flasks a, b, c, e, and f. The amount of water had been adjusted to allow for the volume of acid and the calcium hydroxide slurry. The mixture in each flask was mixed thoroughly. Each of the reaction flasks was chilled in an ice bath and the temperature of the mixture in the reaction flask was about 8–12° C. The mixture was continuously stirred at a rate of about 700 rpm.

Separately, a slurry was made by adding RO/DI water to 4 kg of calcium hydroxide (FCC Grace, 98% purity) making a final volume of 8 L. The mole ratio of calcium hydroxide to concentrated sulfuric acid was determined to be 0.45 to 1 from FIG. 1. The slurry was a 50% (W/V) mixture of calcium hydroxide in water. The slurry was mixed well with a high-shear-force mixer until the slurry appeared uniform. The slurry was then chilled to about 8–12° C. in an ice bath and continuous stirred at about 700 rpm.

To each of the reaction flasks was added 150 ml of the calcium hydroxide slurry every 20 minutes until 1.276 L (i.e.

638 g dry weight, 8.61 moles, of calcium hydroxide) of the slurry had been added to each reaction vessel. The addition was again accompanied by well mixing at about 700 rpm.

After the completion of the addition of the calcium hydroxide to the reaction mixture in each reaction vessel, the mixture was filtered through a 5-micron filter.

The filtrate was allowed to sit for 12 hours, the clear solution was decanted to discard any precipitate formed. The resulting product was AGIIS having an acid normality of 1.2–1.5.

EXAMPLE 2
Preparation of 2 N AGIIS ($H_2SO_4$/Ca $(OH)_2$/$CaSO_4$)

For the preparation of 1 L of 2 N AGIIS, an amount of 79.54 ml (1.44 moles, after purity adjustment and taking into account the amount of acid to be neutralized by base) of concentrated sulfuric acid (FCC Grade, 95–98% purity) was slowly added, with stirring, to 853.93 ml of RO/DI water in a 2 L reaction flask. Five gram of calcium sulfate (FCC Grade, 95% purity) was then added slowly and with stirring to the reaction flask. The mixture was mixed thoroughly. At the point, the mixture would usually indicated an acid normality of 2.88. The reaction flask was chilled in an ice bath and the temperature of the mixture in the reaction flask was about 8–12° C. The mixture was continuously stirred at a rate of about 700 rpm.

Separately, a slurry was made by adding 49.89 ml of RO/DI water to 33.26 g (0.44 mole, after purity adjustment) of calcium hydroxide (FCC Grace, 98% purity) making a final volume of 66.53 ml. The mole ratio of calcium hydroxide to concentrated sulfuric acid was determined to be 0.44 to 1 from FIG. 1. The slurry was mixed well with a high-shear-force mixer until the slurry appeared uniform. The slurry was then chilled to about 8–12° C. in an ice bath and continuous stirred at about 700 rpm.

The slurry was then slowly added over a period of 2–3 hours to the mixture, still chilled in an ice bath and being stirred at about 700 rpm.

After the completion of the addition of slurry to the mixture, the product was filtered through a 5-micron filter. It was normal to observe a 20% loss in volume of the mixture due to the retention of the solution by the salt and removal of the salt.

The filtrate was allow to sit for 12 hours, the clear solution was decanted to discard any precipitate formed. The resulting product was AGIIS having an acid normality of 2.

EXAMPLE 3
Preparation of 12 N AGIIS ($H_2SO_4$/Ca$(OH)_2$/$CaSO_4$)

For the preparation of 1 L of 12 N AGIIS, an amount of 434.17 ml (7.86 moles, after purity adjustment and taking into account amount of acid neutralized by base) of concentrated sulfuric acid (FCC Grade, 95–98% purity) was slowly added, with stirring, to 284.60 ml of RO/DI water in a 2 L reaction flask. Three gram of calcium sulfate (FCC Grade, 95% purity) was then added slowly and with stirring to the reaction flask. The mixture was mixed thoroughly. The reaction flask was chilled in an ice bath and the temperature of the mixture in the reaction flask was about 8–12° C. The mixture was continuously stirred at a rate of about 700 rpm.

Separately, a slurry was made by adding 210.92 ml of RO/DI water to 140.61 g (1.86 moles, after purity adjustment) of calcium hydroxide (FCC Grace, 98% purity) making a final volume of 281.23 ml. The mole ratio of calcium hydroxide to concentrated sulfuric acid was determined to be 0.31 from FIG. 1. The slurry was mixed well with a high-shear-force mixer until the slurry appeared uniform. The slurry was then chilled to about 8–12° C. in an ice bath and continuous stirred at about 700 rpm.

The slurry was then slowly added over a period of 2–3 hours to the mixture, still chilled in an ice bath and being stirred at about 700 rpm.

After the completion of the addition of slurry to the mixture, the product was filtered through a 5-micron filter. It was normal to observe a 20% loss in volume of the mixture due to the retention of the solution by the salt and removal of the salt.

The filtrate was allow to sit for 12 hours, the clear solution was decanted to discard any precipitate formed. The resulting product was AGIIS having an acid normality of 12.

EXAMPLE 4
The Effects of AGIIS on Cold Sores

A forty-five year old white male discovered cold sores on his upper lip on day 1. He applied AGIIS, 4N, pH –0.6, pH 1.8, to a cotton ball and "soaked" the sores for approximately one minute twice on day 1 and day 2. On day 3 he applied the AGIIS four times at various times throughout the day.

The slight pain that the cold sores caused was greatly reduced, almost immediately, upon applying the AGIIS to the sores. By the end of the third day of application the cold sores were virtually gone. Normally, it takes about seven days for the subject to heal cold sores using medication given to him by his physician.

AGIIS can be a useful treatment for cold sores due to herpes simplex.

AGIIS solution used in Examples 5 through Example 30 below was prepared by mixing concentrated sulfuric acid with either calcium hydride or calcium metal.

EXAMPLE 5
The Effects of AGIIS on Blade Shaver Cuts

A forty-five year old white male cut his face using a blade shaver in three locations. He applied the AGIIS, pH 1.8, with a "soaked" cotton ball directly to the cuts.

The cuts stopped bleeding within twenty seconds and the pain stopped almost immediately.

AGIIS can be useful as a cutaneous coagulant.

EXAMPLE 6
Decontamination of Portable Water

Portable water contained non coliform organisms. AGIIS, pH 1.8, was added to this water to bring the pH to 2.0. There was no growth when the water was cultured, and the water could be consumed without adverse effects.

EXAMPLE 7
The Effects of AGIIS on Plague and Bacteria

A forty-five year old white male with orthodontic appliances rinsed his mouth and teeth with AGIIS for 37 days. He used approximately 10 mL of AGIIS, pH 1.8, one to two times daily. He rinsed in the morning and sometimes prior to going to bed. He continued to brush his teeth twice per day and used an OTC mouthwash following the brushing.

He noticed that the surface of his teeth was not coated with a film as he had experienced prior to using AGIIS. He stated his mouth seemed to remain fresher for a longer period of time. He also noticed that his teeth seemed to be whiter and brighter. He received a dental cleaning on day 37. The hygienist performed a series of tests to evaluate the general condition of this teeth. The hygienist applied a dye to his teeth that allowed the hygienist to see plaque and/or bacteria that were present on his teeth. The hygienist used a computer with a video camera to view and record the condition of his teeth. The result showed that the top two thirds of his teeth showed virtually no plaque and no bacteria. The bottom one third that touches the gum area showed minor amounts of plaque and bacteria. The gums were determined to be in excellent condition. The hygienist suggested that the subject should wash with the AGIIS at least as often as he uses mouthwash and concentrate on bathing the gum area. The hygienist will continue to follow the progress. The hygienist also used a chemical and an ultraviolet light to determine if the AGIIS was removing tooth enamel. The study indicated that the AGIIS was not removing enamel.

AGIIS appears to help remove plaque and bacteria from the subjects teeth and mouth, whiten the teeth and kept his mouth fresher for a longer period of time without apparent removal of tooth enamel.

EXAMPLE 8
Effect of AGIIS on a Tumor

A 50 year old man with multiple epidermoid cyst was topically treated with pH 1 AGIIS. Two tumor sites were selected and treated; however, there was no effect after 3 days. Then 0.1 mL of pH 1 AGIIS was injected intratumor via a 27 gauge needle and a tuberculin syringe. Within 24 hours the mass was gone and only a small scab where the mass was attached to the skin remained. There were no adverse effects and only slight stinging accompanied the injection. The scab at the tumor sight was gone in 7 days.

EXAMPLE 9
Effect of AGIIS on the Tissues of a Heparinized Dog

A 15 kg male beagle dog was scheduled for liver harvest to provide primary canine hepatocytes for toxicology tissue culture screening. The dog was prepared by having food withdrawn 24 hours prior to study. The dog was anesthetized by 2 mL of sodium pentothal and heparinized by injecting 5 mL, 1000 units/mL, heparin IV. Liver harvest was completed and various organs and skin incisions were exposed to an aqueous solution of a AGIIS having a pH value of 1. There were no adverse effects on the tissues exposed to the AGIIS. Heparinized blood placed in contact with AGIIS became brown and granular in color and consistency. There was no effect on clotting time in the heparinized dog.

EXAMPLE 10
Effect of AGIIS on Surgical/Wounds in a Rabbit

A male rabbit was anesthesitized with 3 mL Ketamine IM, and his abdomen was shaved. Both sides of the abdomen were numbered with a permanent blue marker in the following sequence: 1, 2, 3, 4, 5, C where 1=pH 1, 2=pH 2, 3=pH 3, 4=water for irrigation ("WFI"), 5=air control and C=clotting time control. The pH 1, 2, and 3 designate aqueous solutions of AGIIS having pH of 1, 2, and 3, respectively, or abbreviated as "pH 1 AGIIS treated" or "pH 1 treated," etc. Six incisions, 1 cm wide, were made at 2 different times. Various fluids corresponding to the labeled incision were introduced into the corresponding wound and the results observed for at least 20 minutes. Clotting times were determined by capillary tube fibrin method and found to be normal. Air control wounds clotted in about 2.5 minutes. Water for irrigation treated wounds appeared to have an extended clotting time of about 3 to 4 minutes duration. Wounds treated with an aqueous solution of AGIIS with pH 3 were not significantly different from WFI treated wounds. Wounds treated with an aqueous solution of AGIIS with pH 2 clotted in less than 2 minutes. Wounds treated with an aqueous solution of AGIIS with pH 1 clotted within 30 seconds and the clots assumed a dark brown halo around the periphery of the wound. By 5 minutes this wound was completely dry while all other wounds continued to ooze serum/lymph. All wounds were observed at 10 & 20 minutes. There were no differences noted at these observation times between the controls, WFI and pH 3 AGIIS treated wounds. At 20 minutes, the pH 2 treated wound was moist, but had contracted 10 mm as measured side to side. The pH 1 treated wound was dry with brown pigmented clots around the periphery of the wound. This wound had contracted 25 mm and the subcutaneous tissues were light brown in color. This pigment was supposed to be hemosiderin which is the iron precipitant from the blood cells coming in contact with the AGIIS. Also of interest were the blood clots, while being brown on the outside were red and normal in appearance on the inside. All wounds were sutured with a 3-0 Vicryl® mattress suture. Skin apposition was easier in the pH 1 AGIIS treated wound as the skin edges seemed to stick together as the suture was tied.

On the following day the incisions were examined and photographed. The incision treated with pH 1 AGIIS was more inflamed than the other incisions; however, it was completely closed. Only a small amount of pulling on the other incisions caused them to open, but equal and even increased tugging did not open the pH 1 AGIIS treated incisions. This finding was not expected. The tissue junction was dry and adhered. The rabbit was examined without anesthesia and did not display undue discomfort. There did not appear to be any effect on the synthetic Vicryl® suture material.

EXAMPLE 11
Effect of AGIIS on the Opthalmic Tissues of a Rabbit

The pH 1 and pH 2 AGIIS material was placed in the left and right eye respectively of a New Zealand white rabbit. At the 10 minute observation, there appeared to be more redness in both eyes than normal; however, the rabbit did not and was not experiencing discomfort. At the 20 minute observation, there continued to be an increase in redness, but the eyes appeared normal. At the 1 hour observation, the eyes were slightly redder than normal, but the rabbit was not tearing or in discomfort. The rabbit was returned to his cage.

The above mentioned New Zealand white rabbit was examined approximately 24 hours post treatment. The eyes were examined and appeared normal. There was no evidence of corneal ulceration, opacity, or tearing.

EXAMPLE 12
Effect and Use of AGIIS During a Surgical Procedure

A 47 pound mixed female bull dog was presented for ovariohysterectomy. The dog was anesthetized with 10 mL (50 mg/mL) pentabarbatol sodium and intubated. The incision site was prepared with an alcohol and Betadine scrub. The incision was made with a #10 steel surgical blade. Large blood vessels were controlled with hemostats. An aqueous solution of AGIIS having pH of 1 was dropped via syringe onto small bleeding cutaneous vessels. While the hemorrhage was not stopped immediately, the tissues surrounding the vessels contracted exposing the bleeding vessels and facilitated their mechanical clamping. Very small vessels clotted immediately, as seen in the rabbit, and tissue fluid seepage into the surgical field was controlled. The ovaries and uterine horns were removed. Two to four drops of the aqueous solution of AGIIS (pH=1) were placed on the surgical stumps of the uterus and ovarian pedicles. Tissue color changed to slightly brown in tint, but there were no other tissue effects. The pH 1 AGIIS did not seem to have any effect on the peritoneal or serrosal surfaces of the abdominal organs. The skin edges of the incision were treated with pH 1 AGIIS prior to dog's closure. The closure with 2-0 Vicryl® was routine. The dog was examined 24 hours later and the recovery and incision appeared normal. There were no adverse effects seen at the skin closure edges and the wound was sealed. The skin closure had a cosmetic appearance. Use of the pH 1 AGIIS did not appear to have any adverse effects on the surgically exposed tissues. It appeared to be effective in controlling hemorrhage in vessels less than 1 mm in outside diameter and lymphatics. Additionally, the AGIIS product rapidly removed blood from the surgical instruments.

EXAMPLE 13
Investigation of pH 1.4 AGIIS to Remove Endotoxins from Glass Surfaces Glass tubes were coated with BSA and autoclaved. Tube contents were removed and culture media along with $E.$ $coli$ 0157:H7 organisms were placed in the tubes. After incubation the tubes were autoclaved and the cycle was repeated in order to coat the tubes with endotoxins.

Tubes were divided into two groups: Group 1 tubes were filled with endotoxin free LAL water. Group II tubes was filled with pH 1.4 AGIIS solution. All tubes were then boiled for 20 minutes. After boiling endotoxin free LAL water was introduced into each tube and the tubes were vortexed vigorously. The contents of each tube were assayed for endotoxins using an LAL Test Kit.

Testament with the pH 1.4 AGIIS solution decreased the associated endotoxin level from 22.66 EU/mL to undetectable levels (<0.03 EU/mL). Treatment with LAL reagent water only did not reduce the endotoxin level associated with the glass tubes.

EXAMPLE 14
Investigation of pH 1.4 AGIIS to Remove Endotoxins from Plastic Medical Devices Plastic test tubes were coated with endotoxins by repeated culture with $E.$ $coli$ 0157:H7 suspended in a beef suspension and autoclaving after each cycle. Tubes were divided into two groups. Group 1 tubes; boiled with endotoxin free LAL water. Group II tubes room temperature. Group III tubes; boiled with a pH 1.4 AGIIS solution. Treatment with the pH 1.4 AGIIS solution decreased the tube associated endotoxin level from ~45 EU/mL to undetectable levels (<0.03 EU/mL) or an ~256 fold reduction.

EXAMPLE 15
Investigation of pH 1.4 AGIIS to Remove Endotoxins from Stainless Steel Surfaces Stainless steel slabs (SSS) were coated with endotoxins by repeated culture with $E.$ $coli$ 0157:H7 and autoclaving after each cycle. SSS were divided into two groups: Group 1 slabs were boiled with endotoxin LAL water. Group II coupons were boiled with a pH 1.4 AGIIS solution.

Treatment with the pH 1.4 AGIIS solution decreased the SSS associated endotoxin level from 4 EU/mL to undetectable levels (<0.03 EU/mL). Treatment with LAL reagent water did not reduce the endotoxin level associated with the SSS.

EXAMPLE 16
Anti-toxin Effect of AGIIS Treatment

An equal volume of a pH 0.5 solution of AGIIS was added to an $E.$ $coli$ 0157:H7 culture. The resultant pH was ~1.0. The culture was then titrated back to ~pH 7.0 with 5N NaOH. The untreated and treated cultures were checked for Shiga Like Toxin II using Morningstar Diagnostic, Inc. SLT II test. The untreated culture was positive for SLT-II whereas the AGIIS treated culture was negative for SLT-II.

To show that we did not simply destroy all antigens, material from the untreated and AGIIS treated culture were checked for O157 antigens. Both the treated and AGIIS treated cultures were positive for O157 antigens. Therefore, the treatment with AGIIS either inactivated the toxin by destroying or dissociating the toxin to a non-antigenic form.

EXAMPLE 17
Study to Determine if Different pH Solutions of AGIIS have Distinct Effects on the Oxidation of Bananas Bananas were peeled and immersed in AGIIS solutions having a pH of 1.2, 1.4, 1.6, 1.8 or 2.0, respectively, for 5 min.

Oxidation of banana pieces was noticeable depressed by treatment with AGIIS solutions having a pH ranging from 1.2–1.6. After 24 hr bananas pieces treated with pH 1.2 and 1.4 AGIIS were for the most part free of oxidation. Thus low pH AGIIS is more effective at preventing oxidation of banana fruit pieces.

EXAMPLE 18
Study of pH 1.2 AGIIS in Prevention of Oxidation of Apples

Apples were cut in half and immersed in a pH 1.2 solution of AGIIS or in water. After treatment apple halves were removed and incubated at ambient room temperature. At four hours post-treatment apple halves treated with the AGIIS solution were white while the water treated apple halves were brown due to oxidation. The differences were still apparent 24 hr later.

EXAMPLE 19
Study of pH 0.56 AGIIS in Removal of Oxidation from Brass Metal

Brass items were bathed in AGIIS solution and hard to remove oxidation was removed by scrubbing with stainless steel pads. Oxidation that accumulated over a twenty-year period was removed with minimal effort.

EXAMPLE 20
Study of pH 0.56-AGIIS Solution in Decreasing the pH of a Sulfuric Acid Solution Sulfuric acid was diluted to a pH 2.3 using deionized water (~700 mL). AGIIS solution added in 1 mL aliquots. pH went down in increments from 2.3 to 1.56. Therefore, a pH 0.56 solution of AGIIS could be used to increase the acidity of a sulfuric acid solution.

EXAMPLE 21
Study to Determine the Concentration of a pH 0.45 AGIIS Solution

AGIIS (50 mL) was placed in an erlenmeyer and KOH or NaOH of known concentration (usually 1 N NaOH) was added to determine the "acidic" concentration of the AGIIS. Titration gave a value of 1.84 N. When base was added, the pH decreased from 0.45 to 0.35 and then increased steadily until neutrality was reached suggesting the dissociation of hydronium complexes in the presence of base to yield additional hydronium ions.

EXAMPLE 22
Study to Ascess the Effect of the Addition of AGIIS on the Organoleptic Properties of Wines Cups were filled with 30 mL of wine. One hundred (100) microtiters of AGIIS (pH 0.3), were added to half of the cups and, 100 microliters of deionized water, were added to the other half. A blinded panel of tasters was asked to taste the wine.

Changes in the organoleptic properties were noted. In particular, all tasters agreed the wine supplemented with AGIIS was less bitter. Color and pH of the wine were unchanged.

EXAMPLE 23
Study to Determine the Effect of AGIIS on Concrete and Tile Surfaces AGIIS applied at an ambient and elevated temperature to concrete removed grime and left the concrete between the stones whiter. The heated AGIIS was more effective than the ambient temperature AGIIS.

AGIIS applied to algae coated concrete killed and removed the algae.

Calcium carbonate deposits on swimming pool tiles were dissolved when AGIIS was applied.

AGIIS seems to be an effective agent for cleaning concrete surfaces without the corrosive effects of muriatic acid.

EXAMPLE 24
Study to Determine if AGIIS Binds to Bran

Four 100-mL cups were filled with wheat bran. Two of the cups were filled with a pH 0.8 AGIIS solution while the remaining cups were filled with deionized water. The bran was allowed to rehydrate for 1 hr and all cups were then placed in a −84° C. freezer. Frozen cups were then placed in a lyophilizer for 24 hr.

After lyophilization the contents of each cup were removed and transferred to a 500-mL beaker. One hundred and fifty mL of pH 7 deionized water was added to each beaker and the freeze-dried bran was allowed to rehydrate.

Bran treated with AGIIS readily rehydrated and/or dissolved. Whereas the water treated bran had to be physically broken up before it dissolved.

When all samples were rehydrated, the pH of each sample was determined. The average pH of the bran treated with water was 5.8 whereas the pH of the AGIIS treated bran was 2.84. Thus AGIIS treatment lowered the pH of the treated bran and changed the rehydration characteristics of the bran.

EXAMPLE 25
Effect of AGIIS on Oxidation of Avocados

Avocados were peeled and sliced into pieces. Individual pieces were immersed in AGIIS solutions having a pH of 1.2, 1.4, 1.6, 1.8 or 2.0, respectively, for 10 min. After incubation at ambient room temperature on an open shelf for 8 hrs, strong oxidation of pieces treated with pH 1.4–2.0 was evident. However, pieces treated with a pH 1.2 solution of AGIIS were free of oxidation and looked freshly cut.

EXAMPLE 26
Study of the Effect on the Organoleptic Properties of Ketchup by Addition of AGIIS Eighty milliliters of ketchup were placed in 100-mL cups. Five mL of deionized water was added to half of the cups. Five mL of AGIIS (~pH 0.5) was added to the other cups.

The cup contents were thoroughly mixed and a blinded panel of taste testers was asked to give their opinions and selection as to taste.

The AGIIS treated ketchup retained a thick consistency and the color stayed an intense red. Moreover, it was also determined that the taste was enhanced. The water treated ketchup lost consistency, color diminished and taste was judged not as good.

EXAMPLE 27
Study of the Effect of AGIIS on a Plant Source of Pharmaceuticals Freshly harvested aloe Vera leaf was dissected to expose the mucilaginous gel in the center of the leaf. Two sections were treated with AGIIS pH 2, and placed in an observation dish. Two other sections were treated with water and placed in an identical observation dish. After 10 minutes at room temperature, the water-treated aloe gel was discolored and appeared brown. The AGIIS-treated aloe gel retained its fresh-cut appearance. After 20 minutes at room temperature, the differences were even more pronounced. The water-treated gel began to liquify, while the AGIIS-treated gel retained its integrity. After four hours at room temperature, the differences were even much more pronounced, and the AGIIS-treated gel still appeared freshly cut.

EXAMPLE 28
Effect of AGIIS on Contaminated Water

Bacteria present in 500 mL of tap water were concentrated by centrifugation at 5000×g for 20 min. Another 500 mL of tap water was titrated to pH 2 using AGIIS solution of pH 0.5. Bacteria in the treated tap water was concentrated by centrifugation at 5000×g for 20 min. Bacteria from each were suspended using 1.5 mL of the AGIIS or tap water and plated to determine the number of viable bacteria in each sample. Treatment with a pH 2 solution of AGIIS reduced the level of viable organism in the water.

EXAMPLE 29
Effect of AGIIS on Street Puddle Water

Water was collected from a puddle at the corner in front of a laboratory building. It was determined that the pH of the water was 7.4. Water was mixed 1:1 with a pH 2 AGIIS solution or sterile saline and treated at ambient room temperature. Following treatement, an aliquot of the AGIIS- and saline-treated water was serially diluted and plated to determine the number of viable organisms. AGIIS treatment effectively decreased the number of viable organism relative to the control of saline.

EXAMPLE 30
Effect of AGIIS on Level of Viable Microbes on a Lettuce Head

Lettuce leafs were stripped from lettuce heads and placed in two groups. Group I lettuce leafs were treated with a pH 2 solution of AGIIS for 3 min and then stomached in sterile saline. Group II leafs were treated with saline for 3 min then stomached. An aliquot from each group was serially diluted and each dilution was plated to determine the number of viable organisms present following treatment. The number of viable organisms associated with a pH 2 solution of AGIIS was decreased compared to that of the control.

EXAMPLE 31

Effect of AGIIS On hydrolysis of Chicken Feed AGIIS was found to convert complex, carbohydrates in chicken feed to monosaccharides which were much easier to digest than the complex carbohydrates in the stomach. The chicken feed was obtained from a commercial broiler producer. This grower ration contained 26% protein and was yellow corn based. The chicken feed was digested with 2 N of AGIIS at a temperature of 85° C. for different length of time. AGIIS was prepared by $H_2SO_4/Ca(OH)_2/CaSO_4$ method. Modified Fehling's solution method was employed to determine the amount of reducing sugar produced during the reaction. Controls using de-ionized water were performed in parallel. From the result given below, it can be seen that chicken treated with AGIIS had higher amount of reducing sugar which is easier than complex carbohydrate for chicken to digest.

| Sample Weight (g) | Reaction Time (hour) | Amount of Reducing Sugar (%) | |
|---|---|---|---|
| | | AGIIS | Control |
| 15 | 1 | 2.96 | 0.2 |
| 20 | 1 | 3.13 | 0 |
| 25 | 1 | 4.85 | 0.1 |
| 30 | 1 | 4.96 | 0.2 |
| 40 | 1 | 6.5 | 0.16 |
| 40 | 2 | 8.1 | 0 |
| 40 | 3 | 10.9 | 0 |
| 40 | 4 | 14.2 | 0.33 |
| 40 | 5 | 15.5 | 0.35 |
| 50 | 1 | 6.2 | 0.26 |

EXAMPLE 32

Charring of Sucrose by Various Agents

Sulfuric acid having a concentration of 19 N or higher will char or "dehydrate" sucrose. This reaction was visible and could be used as a measurement parameter. Results with sulfuric acid of less than 19 N was harder to interpret due to the extended duration of the reaction. Roughly, the charring reaction could be divided into three stages.

The first stage was the initial color change. This usually occurred within the first two minutes of the reaction at room temperature. The first stage was characterized by color change in sucrose, i.e. the white color of sucrose turned into light yellow. Most acidic reagents used in this experiment would turn the color of sucrose into light yellow within the first two minutes of contact.

The second stage was the blackening of the sucrose.

The third stage was the charring or complete "burning" of sucrose. At this stage, heat was generated and vapor was given off. The reaction could be violent and mildly explosive depending on the concentration of the acid.

Given below is a table summarizing the results from comparative charring experiments of solutions of: (1) AGIIS; (2) $H_2SO_4$; and (3) $H_2SO_4*CaSO_4$. The solution of AGIIS was prepared by the reaction of calcium hydroxide with sulfuric acid having added calcium sulfate therein. Solution (3), i.e. $H_2SO_4*CaSO_4$, was a solution of sulfuric acid saturated with calcium sulfate. The data were compiled from experiments carried out at room temperature.

| Solution | Initial Change | Time to Blacken | Time to Char |
|---|---|---|---|
| 5N AGIIS | No change | No change | Not Detected |
| 5N $H_2SO_4*CaSO_4$ | No change | No change | Not Detected |
| 5N $H_2SO_4$ | No change | No change | Not Detected |
| 10N AGIIS | >24 Hours | >24 Hours | Not Detected |
| 10N $H_2SO_4*CaSO_4$ | >24 Hours | >24 Hours | Not Detected |
| 10N $H_2SO_4$ | >24 Hours | >24 Hours | Not Detected |
| 19N AGIIS | >20 min | ~Hour | Not Detected |
| 19N $H_2SO_4*CaSO_4$ | <2 min | <1 Hour | Not Detected |
| 19N $H_2SO_4$ | 40 sec | 25 min | Not Detected |
| 27N AGIIS | 2 min | <10 min | Not Detected |
| 27N $H_2SO_4*CaSO_4$ | <2 min | <6 min | >10 min |
| 27N $H_2SO_4$ | Instant | <1 min | >10 min |
| 28N AGIIS | <2 min | <10 min | Not Detected |
| 28N $H_2SO_4*CaSO_4$ | <1 min | <5 min | <10 min |
| 28N $H_2SO_4$ | Instant | <1 min | <10 min |
| 29N AGIIS | 1 min | <8 min | Not Detected |
| 29N $H_2SO_4*CaSO_4$ | Instant | <5 min | <8 min |
| 29N $H_2SO_4$ | Instant | <1 min | <6 min |

AGIIS, if prepared correctly, would cause the color of sucrose to remain yellow and only slowly darken over the next 7 or 8 minutes. AGIIS having an acid normality of between 27 and 29 N, if prepared incorrectly, will darken the color of sucrose in less than about 5 minutes. Further, the charring of the sucrose by properly prepared AGIIS, even at acid normality of 29 N, was not be detected more than 24 hours later at room temperature.

In contrast, as shown in the Table, either sulfuric acid or sulfuric acid saturated with calcium sulfate, under same acid normality, will char sucrose much more rapidly than AGIIS at room temperature.

EXAMPLE 33

Non-Volatility and Non-Corrosiveness of AGIIS

AGIIS prepared was non-volatile at room temperature. Even as concentrated as 29 N, the AGIIS had no odor, did not give off fumes in the air, and was not irritating to a human nose when one smelled the concentrated solution. When concentrated AGIIS was diluted with water, very little heat was given off, while dilution of concentrated sulfuric acid with water gave off a large amount of heat, i.e. very exothermic.

A human skin would get very hot upon contacting a solution of 28 N of sulfuric acid saturated with calcium sulfate. The solution was irritating to the skin within a few minutes, and chemical burn will follow. Sulfuric acid, 28 N, would chemically burn a human skin within less than one minute.

In contrast, upon contacting a human skin, a solution of AGIIS having an acid normality of 28 N, would cause only a mildly warm sensation. There was no irritating effects and the solution did not cause chemical burn even after about minutes at room temperature on the skin.

What is claimed is:

1. A method for manufacturing a prepared nutriment comprising:

contacting AGIIS with a nutriment material, wherein the AGIIS is isolated from a mixture comprising sulfuric acid and calcium hydroxide, or a calcium salt, or a mixture of the two, wherein when the AGIIS is isolated from a mixture comprising sulfuric acid and calcium hydroxide then the mole ratio of calcium hydroxide to sulfuric acid ranges from about 0.1 to about 0.5, and wherein the AGIIS has a pH of less than about 2.

2. A method for manufacturing a prepared nutriment comprising:

contacting AGIIS with a carrier to give a constituted carrier; and blending the constituted carrier with a nutriment material, wherein the AGIIS is isolated from a mixture comprising sulfuric acid and calcium hydroxide, or a calcium salt, or a mixture of the two, wherein when the AGIIS is isolated from a mixture comprising sulfuric acid and calcium hydroxide then the mole ratio of calcium hydroxide to sulfuric acid ranges from about 0.1 to about 0.5, and wherein the AGIIS has a pH of less than about 2.

3. A method for incorporating AGIIS into a dry nutriment, comprising:

adding AGIIS to a suitable carrier to give a premixed product, and blending the premixed product with the dry nutriment, wherein the AGIIS is isolated from a mixture comprising sulfuric acid and calcium hydroxide, or a calcium salt, or a mixture of the two, wherein when the AGIIS is isolated from a mixture comprising sulfuric acid and calcium hydroxide then the mole ratio of calcium hydroxide to sulfuric acid ranges from about 0.1 to about 0.5, and wherein the AGIIS has a pH of less than about 2.

4. The method of claim 3, wherein the AGIIS is prepared by mixing calcium hydroxide with sulfuric acid with or without calcium sulfate added thereto, and the AGIIS having a certain acid normality is less effective in charring sucrose and less corrosive to an animal skin than a saturated solution of calcium sulfate in sulfuric acid having the same acid normality, and wherein the AGIIS is non-volatile at room temperature and pressure.

5. The method of claim 3, wherein the suitable carrier is a methylcellulose, a psyllium, bran, rice hull or corn gluten.

* * * * *